(12) United States Patent
Galluseder et al.

(10) Patent No.: US 11,318,002 B2
(45) Date of Patent: May 3, 2022

(54) MEDICAL OR DENTAL CLEANING AND/OR CARE DEVICE

(71) Applicant: W&H Dentalwerk Bürmoos GmbH, Bürmoos (AT)

(72) Inventors: Florian Galluseder, Tarsdorf (AT); Jürgen Meburger, Lamprechtshausen (AT); Johann Eibl, Mattighofen (AT)

(73) Assignee: W&H Dentalwerk Bürmoos GmbH, Bürmoos (AT)

( * ) Notice: Subject to any disclaimer, the term of this patent is extended or adjusted under 35 U.S.C. 154(b) by 196 days.

(21) Appl. No.: 16/353,815

(22) Filed: Mar. 14, 2019

(65) Prior Publication Data
US 2019/0209279 A1    Jul. 11, 2019

Related U.S. Application Data

(63) Continuation of application No. PCT/EP2017/073531, filed on Sep. 19, 2017.

(30) Foreign Application Priority Data

Sep. 19, 2016  (EP) ..................................... 16189432

(51) Int. Cl.
*A61C 19/00*  (2006.01)
*A61L 2/24*  (2006.01)
(Continued)

(52) U.S. Cl.
CPC ............ *A61C 19/002* (2013.01); *A61B 90/70* (2016.02); *A61L 2/00* (2013.01); *A61L 2/16* (2013.01);
(Continued)

(58) Field of Classification Search
CPC . A61C 19/002; A61L 2/16; A61L 2/00; A61L 2/24; A61L 2202/14; A61L 2202/122; A61L 2202/24; A61B 90/70
See application file for complete search history.

(56) References Cited

U.S. PATENT DOCUMENTS 4,990,087 A * 2/1991 De Rocchis ......... A61C 19/002
433/104
7,850,905 B2 * 12/2010 Petersen ................ A61B 90/70
422/2

(Continued)

FOREIGN PATENT DOCUMENTS

| DE | 102014103071 | 9/2014 |
| EP | 2364665 | 9/2011 |
| JP | 2014534851 A | 12/2014 |

OTHER PUBLICATIONS

International Search Report for PCT/EP2017/073531, dated Dec. 1, 2017.

*Primary Examiner* — Regina M Yoo
(74) *Attorney, Agent, or Firm* — Klarquist Sparkman, LLP (57) ABSTRACT

Medical or dental cleaning and/or care device for cleaning and/or care of at least one instrument, comprising: a housing, a plurality of chambers, each of the plurality of chambers configured to accommodate at least one instrument, wherein each chamber has at least one dispensing element for dispensing at least one cleaning agent and/or care agent into the respective chamber and/or to the instrument accommodated in the respective chamber, an opening in the housing, through which the plurality of chambers can be loaded with instruments, and a cover for closing the opening and the plurality of chambers, wherein only a part of the opening can be closed by the cover so that when at least one of the plurality of chambers is completely closed, at least (Continued)

another one of the plurality of chambers is not completely closed.

20 Claims, 2 Drawing Sheets

(51) Int. Cl.
*A61B 90/70* (2016.01)
*A61L 2/16* (2006.01)
*A61L 2/00* (2006.01)

(52) U.S. Cl.
CPC ............ *A61L 2/24* (2013.01); *A61L 2202/122* (2013.01); *A61L 2202/14* (2013.01); *A61L 2202/24* (2013.01)

(56) References Cited

U.S. PATENT DOCUMENTS

| | | |
|---|---|---|
| 2013/0092192 A1 | 4/2013 | Pfaffinger et al. |
| 2013/0098407 A1 | 4/2013 | Perlman et al. |
| 2018/0228341 A1* | 8/2018 | Stojalowski .............. B08B 3/02 |

* cited by examiner

MEDICAL OR DENTAL CLEANING AND/OR CARE DEVICE

CROSS REFERENCE TO RELATED APPLICATION

This application is a U.S. bypass continuation application of International Application No. PCT/EP2017/073531, filed Sep. 19, 2017, which in turn claims priority from pending European Patent Application No. 16189432.4, filed Sep. 19, 2016, which are incorporated herein by reference.

FIELD

The present invention relates to a medical or dental cleaning and/or care device for cleaning and/or care of at least one medical or dental instrument.

BACKGROUND

European Patent Application EP 2 364 665 A1 describes a medical or dental cleaning and/or care device having a cleaning chamber, into which several instruments to be cleaned or cared for can be introduced. Each instrument is connected with a connector to a supply device for supplying a cleaning agent or care agent, wherein the connections are arranged on a base element. The base element is arranged rotatably in the chamber, so that during a cleaning and/or care procedure, a connector with the instrument attached to it is connected to the supply device, while at least one additional connector is not connected to the supply device. With this known cleaning and/or care device, sequential cleaning and/or care of a plurality of instruments introduced into the cleaning chamber is/are possible. As described, all the instruments to be cleaned and/or cared for are first introduced into the cleaning chamber, then the instruments are cleaned and/or cared for in order, and after conclusion of the cleaning and/or care of all the instruments accommodated in the cleaning chamber, these instruments are removed from the cleaning chamber.

SUMMARY

Based on the foregoing it is an object to create an alternative medical or dental cleaning and/or care device, the handling of which is simpler for the user and saves more time.

This object is achieved by a medical or dental cleaning and/or care device for cleaning and/or care of at least one medical or dental instrument and by a method for operation of a medical or dental cleaning and/or care device having the features, described below.

According to an embodiment the medical or dental cleaning and/or care device for cleaning and/or care of at least one medical or dental instrument comprises: a housing, a plurality of chambers, each for accommodating at least one medical or dental instrument to be cleaned and/or cared for, wherein each chamber has at least one dispensing dement for dispensing at least one cleaning agent and/or care agent into the respective chamber and/or to the at least one medical or dental instrument to be cleaned and/or cared for and accommodated in the respective chamber, a (single or joint) opening in the housing, through which the plurality of chambers can be loaded with medical or dental instruments, and a cover for closing the opening and the plurality of chambers, in particular during a cleaning and/or care procedure. Only a portion of the opening can be covered or closed by the cover, so that when at least one (first) chamber of the plurality of chambers is completely closed and in particular is or can be supplied with a cleaning agent and/or care agent, at least one other chamber or one second chamber of the plurality of chambers is not (completely) closed and/or can be loaded with a medical or dental instrument through the opening and thus in particular is not supplied with a cleaning agent and/or care agent.

Thus, preferably at least one (first) chamber of the plurality of chambers is or can be closed completely by the cover while another or a second chamber cannot be completely covered or closed.

Only a portion of the opening can be closed by the cover, so that, alternatively or in addition to the preceding, the cleaning and/or care device, in particular a control or regulating device to be described in greater detail below, is configured to deliver a cleaning agent and/or care agent in or to only one chamber of the plurality of chambers, which is completely closed, while another chamber that is not completely closed is not supplied with a cleaning agent and/or care agent.

Therefore, a medical or dental cleaning and/or care device that can be operated or loaded sequentially and/or in alternation for cleaning and/or care of at least one medical or dental instrument is created in which continuous work is possible in an advantageous manner: while a medical or dental instrument is being supplied with a cleaning agent and/or care agent or cleaned and/or cared for in at least one (completely closed) chamber, a user can remove an instrument that has already been cleaned and/or cared for from another chamber (that is accessible or is not completely closed) and can then load this chamber with another instrument to be cleaned and/or cared for.

The medical or dental cleaning and/or care device is preferably configured to supply a medical or dental instrument, in particular its interior and/or components arranged in the interior with at least one cleaning and/or disinfection and/or lubricating agent via the dispensing elements. The medical or dental cleaning and/or care device is preferably configured to clean and/or flush an element provided in the medical or dental instrument, a line, a channel or a tube, for example, for the transport of gas, liquids, air or water, with a cleaning agent and/or disinfectant. The medical or dental cleaning and/or care device is preferably configured to supply a lubricant to moving parts of a medical or dental instrument, in particular bearing elements, for example, ball bearings.

The medical or dental cleaning and/or care device is preferably configured to clean and/or care for a medical or dental instrument in a cleaning or care procedure of short duration. The cleaning and/or care procedure lasts, for example, less than 60 seconds, preferably less than 30 seconds, in particular less than 20 seconds, especially preferably approximately 10 seconds.

The medical or dental cleaning and/or care device preferably comprises a supply device configured to supply at least one cleaning agent and/or care agent to the dispensing elements of the chambers. The supply device preferably connects the dispensing element to sources for the cleaning agent and/or care agent, for example, to containers for the cleaning agent and/or care agent. The supply device preferably includes lines, tubes and/or channels for connecting the cleaning agent and/or care agent sources to the dispensing elements. The supply device preferably includes at least one control element, for example, at least one valve, one throttle or one pump for controlled and/or regulated delivery of a cleaning agent and/or care agent. The supply device preferably includes at least one detector element or sensor element which is configured to detect at least one control variable or one condition of an element of the supply device, for example, an open position of a valve, the delivery rate of a pump or the filling level of a cleaning agent and/or care agent in a container. The supply device preferably includes at least one detector element or sensor element configured to determine a parameter of a cleaning agent and/or care agent, for example, its flow rate, delivery rate, pressure or conductivity.

The supply device is preferably connected to a control or regulating device of the medical or dental cleaning and/or care device. The control or regulating device preferably comprises a microcontroller. The control or regulating device is preferably configured to control and/or regulate the supply device and thus preferably the delivery, in particular the sequential and/or alternating delivery of the at least one cleaning agent and/or care agent into the chambers and/or to the dispensing elements. The control or regulating device is preferably configured to receive and to process a signal of the at least one detector element or sensor element of the supply device and to operate at least one element of the supply device, in particular one of the aforementioned control elements on the basis of this signal. The control or regulating device is especially preferably also operatively connected to a detector unit to be described in greater detail below, which is configured to detect at least one position of the cover.

At least a portion of the supply device and/or the control or regulating device is preferably arranged in the housing of the medical or dental cleaning and/or care device.

The medical or dental cleaning and/or care device preferably comprises two chambers. Alternatively, however, it is also conceivable for the medical or dental cleaning and/or care device to have more than two chambers, for example, three, four, five or n chambers. Each chamber is preferably configured or provided to accommodate a (single) instrument to be cleaned and/or cared for. Alternatively, however, it is also conceivable for at least one chamber to be configured or provided to accommodate more than one instrument to be cleaned and/or cared for.

Each chamber preferably comprises a (single) dispensing element for dispensing at least one cleaning agent and/or care agent, to which in particular one instrument or the only instrument per chamber to be cleaned and/or cared for can be connected. Alternatively, however, it is also conceivable for a chamber to have more than one dispensing element, in which case one instrument to be cleaned and/or cared for can be connected to each dispensing element of a chamber.

The dispensing element preferably has at least one borehole, line or channel through which a cleaning agent and/or care agent can be delivered into one of the chambers and/or to an instrument that is to be cleaned and/or cared for and is accommodated in a chamber. The dispensing element is preferably configured to be insert able into a receptacle or a coupling element of an instrument to be cleaned and/or cared for so that the cleaning agent and/or care agent can be delivered into the interior of the instrument. The dispensing element is preferably configured as a tubular connecting pipe which can be inserted in particular into a receptacle or a coupling element of an instrument to be cleaned and/or cared for. The at least one borehole, line or channel of the dispensing element is especially preferably arranged in such a way that it can be connected to a line or channel or tube provided in the medical or dental instrument so that a cleaning agent and/or care agent can be delivered into the line, channel or tube of the medical or dental instrument.

Alternatively, it is also conceivable for the dispensing element to be configured to dispense a cleaning agent and/or care agent to the outside of an instrument to be cleaned and/or cared for. Such a dispensing element preferably includes a nozzle.

According to one embodiment, a medical or dental cleaning and/or care device comprises a first chamber having at least one dispensing element for dispensing a cleaning agent and/or care agent to the outside of an instrument to be cleaned and/or cared for and a second chamber (separate from the first chamber) having at least one dispensing element for insertion into a receptacle or a coupling element of an instrument to be cleaned and/or to be cared for. Alternatively, it is also conceivable for a (single) chamber of the medical or dental cleaning and/or care device to have at least one dispensing element for dispensing a cleaning agent and/or care agent to the outside of an instrument to be cleaned and/or cared for and at least one dispensing element for insertion into a receptacle or a coupling element of an instrument to be cleaned and/or cared for.

The opening in the housing of the medical or dental cleaning and/or care device through which the plurality of chambers can be loaded with medical or dental instruments is configured in particular as a single or joint opening so that all chambers of the cleaning and/or care device in particular are accessible through this opening, i.e., can be loaded with at least one instrument and/or the at least one instrument can be removed therefrom. The opening preferably extends over all chambers of the dental cleaning and/or care device. The opening is preferably provided in the front side of the housing of the cleaning and/or care device. The opening and/or an edge bordering the opening and formed by the housing, for example, and is/are preferably shaped like a rectangle.

The cover for closing the opening and the plurality of chambers during a cleaning and/or care procedure is preferably configured as a door or a lid. The cover, in particular the door or the lid is preferably configured in one piece and/or as a quadrilateral shape, in particular as a rectangle.

As already mentioned above, the cover is preferably of such dimensions that at least one chamber of the plurality of chambers can be closed or covered completely by the cover, while another chamber or the second chamber cannot be closed or covered completely. In other words, the cover is preferably of such dimensions that it does not cover or close all chambers of the cleaning and/or care device at the same time. The area of the cover, in particular the outside or the outer surface of the cover, is preferably smaller than the area of the opening through which the plurality of chambers can be loaded with medical or dental instruments, and/or the area of the opening is larger than the area of the cover. The medical or dental and/or care device especially preferably comprises two chambers, wherein the ratio of the area of the cover to the area of the opening amounts to approximately 1:2.

The plurality of chambers is preferably separated by at least one respective wall element, in particular a fixed or rigid wall element. The at least one wall element is preferably connected to the housing of the cleaning and/or care device or is configured as a part thereof The at least one wall element preferably separates two neighboring chambers from one another, in particular together with the cover, in such a way that no cleaning agent and/or care agent can be transferred from one chamber into another chamber. The at least one wall element is preferably arranged between two dispensing elements or separates them from one another so that in particular only one dispensing element is arranged in each chamber. The at least one wall element is preferably arranged essentially at a right angle to the chamber bottom of a chamber. A groove for removing cleaning agent and/or care agent is preferably provided on the wall element, in particular on a connecting area between the wall element and the chamber bottom. The at least one wall element thus allows sequential and/or alternating operation as well as a clean function of the cleaning and/or care device, in that it prevents a transfer of cleaning agent and/or care agent between the plurality of chambers.

The cover is preferably arranged movably, in particular displaceably, in or on the opening. Alternatively or additionally, the cover can be moved in or along the opening, in particular being displaceable there. The cover is preferably movable or displaceable in a straight line, in particular along or parallel to an edge of the opening or a housing edge which borders the opening. This creates a cover device that is simple to manufacture and is not complicated to operate.

The cover can preferably be moved into a covering or closed position, in particular being displaceable to that position, in which the cover closes or covers (completely) at least one of the plurality of chambers. The cover can preferably be moved, in particular displaced into a plurality of (separate or discrete) covering or closing positions, so that each one of the plurality of chambers can be closed or covered (completely) by the cover. The cover is preferably configured or of such dimensions that it takes only one of the plurality of covering or closing positions and/or closes or covers (completely) only one of the plurality of chambers and/or does not close or cover (completely) at least one of the plurality of chambers. The cover can preferably be moved, in particular can be displaced, into at least one displaced position or intermediate position, in which it does not completely close or cover any of the plurality of chambers. The cover is preferably configured or of such dimensions that in order to move from a first covering position or closed position in which it closes or covers (completely) a first one of the plurality of chambers, into a second covering or closing position in which it (completely) closes or covers another, second one of the plurality of chambers, it takes at least one displaced position or intermediate position.

The opening is preferably bordered by a border (formed by the housing) or by a housing edge on which preferably at least one guide element for moving, in particular for displacing the cover, is provided. The guide element comprises, for example, a strip or a groove. A guide part is preferably provided on the cover, for example, a strip or a groove, wherein the guide part is adapted to the guide element and can be connected to the guide element so that the cover can be moved, in particular displaced in or on the opening. The guide element and the guide groove are in particular intermeshing.

Alternatively or additionally, the border of the housing or the housing edge is configured to limit the movement, in particular the displacement, of the cover. The border or the edge of the housing is configured in particular as a stop for the cover. It is provided in particular that a side edge of the cover and the border or housing edge come in contact with one another to limit the movement, in particular the displacement, of the cover.

The border or the edge of the housing especially preferably has a plurality of sides arranged at an angle to one another, wherein a guide element is provided on at least one (first) side for moving, in particular for displacing, the cover, and another (second) side serves as a stop for the cover. The cover especially preferably has a plurality of sides arranged at an angle to one another, such that a guide element is provided on at least one (first) side for moving, in particular for displacing, the cover, and another (second) side serves as a side edge, which comes in contact with the stop. Due to these features which are defined above, a cover device that is simple to manufacture and uncomplicated to operate is created.

Alternatively or additionally, it is also possible for at least one guide element for moving, in particular for displacing, the cover to be provided on the at least one wall element.

To facilitate operation, at least one handle element is provided on the cover for moving, in particular for displacing, the cover relative to the opening. The at least one handle element comprises, for example, one or more wing-type handle strips. The at least one gripping element protrudes above the housing in particular.

The housing preferably has a front face, in which the opening is provided, wherein the front face comprises a curvature which connects a first front face section which is preferably completely flat and a second front face section which is preferably completely flat, wherein the first front face section and the second front face section are arranged at an angle to one another (at an angle >0°). In addition, the cover has a shape corresponding to front face with a first cover section, which is preferably completely flat, a second cover section, which is preferably completely flat, and a curve connecting the first cover section and the second cover section. The first front face section and the first cover section are preferably configured as skewed planes (with respect to a base surface of the housing of the cleaning and/or care device and/or with respect to the second front face section and/or the second cover section) Thus, the operability of the cleaning and/or care device, in particular the loading and/or removal of the instrument from the plurality of chambers is greatly facilitated.

Each one of the plurality of chambers preferably comprises at least one outlet opening for removing the cleaning agents and/or care agents from the chamber. The at least one outlet opening is preferably arranged in the bottom of a chamber and/or on the at least one wall element. The at least one outlet opening on the at least one wall element preferably comprises one or more slots arranged in the wall element, for example, in the narrow side of the wall element facing the housing opening or in its side wall. The outlet opening is preferably connected to a suction device, which sucks a cleaning agent, and/or care agent present in a chamber through the outlet opening. It is thus advantageously possible, for example, to remove from the chamber any excess cleaning agent and/or care agent that has emerged from an instrument to be cleaned and/or cared for.

According to a preferred embodiment, the medical or dental cleaning and/or care device comprises a detector unit which is configured to detect at least one position of the cover, in particular a cover position or closing position, and to generate a detector signal that is or can be associated with a recognized position. The detector unit is configured in particular to recognize at least one position of the cover in the opening, relative to the opening and/or relative to at least one of the plurality of chambers. The detector unit is especially preferably configured to detect that at least one of the plurality of chambers is completely closed or covered by the cover and/or that the cover is in a covering or closing position. Alternatively or additionally, the detector unit is configured to detect that at least one of the plurality of chambers is not completely closed or covered by the cover.

The detector unit thus advantageously permits simplification and/or automation of the operation of the cleaning and/or care device and increases its operational reliability.

For example, by detecting which one of the plurality of chambers is closed (or not closed) by the cover, the detector unit permits automated supply of a cleaning agent and/or care agent to the at least one closed chamber and/or the at least one dispensing element arranged therein. Accordingly, an automated start of a cleaning and/or care procedure of an instrument is possible as soon as one of the plurality of chambers is closed completely (and optionally a predetermined period of time has elapsed). Accordingly, an immediate automated interruption of delivery of a cleaning agent and/or care agent during a cleaning and/or care procedure is possible if the cover is removed from a completely closed chamber in which a cleaning and/or care procedure is taking place.

The detector unit preferably comprises a magnetic detector unit, for example, a magnetic element and a magnetic sensor, in particular a Hall sensor. Alternatively, however, the detector unit may also comprise any other detectors and may be configured as an inductive, capacitive or optical detector unit, for example.

At least a portion of the detector unit, for example, at least one magnetic element, is preferably provided in or on the cover and can be moved, in particular can be displaced, jointly with the cover. At least a part of the detector unit, for example, at least one magnetic sensor or at least one coil, is preferably arranged in or on the housing so that it is stationary relative to the cover. At least a portion of the detector unit, in particular the part being arranged stationary relative to the cover, is preferably provided several times. A part being arranged stationary, for example, a magnetic sensor or a Hall sensor, is preferably associated with each one of the plurality of chambers.

The detector unit is preferably configured, so that the part of the detector unit that is movable jointly with the cover and the part of the detector unit that is arranged stationary are then positioned next to one another and/or generate a detector signal and/or generate a particularly strong detector signal when at least one of the plurality of chambers is completely closed by the cover and/or can be or is to be supplied with cleaning agent and/or care agent and/or when a side edge of the cover and one border of the housing or the edge of the housing come in contact with one another to limit the movement, in particular the displacement of the cover and/or when the cover assumes a covering or closing position as described above.

The medical or dental cleaning and/or care device preferably comprises a control or regulating device that is operatively connected to the detector unit and is configured to receive and to process the detector signal that is or can be associated with at least one detected position and, on the basis of the received and processed detector signal, to control and/or to regulate the supply of at least one cleaning agent and/or care agent to at least one dispensing element and/or at least one chamber. The control or regulating device is configured in particular to supply at least one cleaning agent and/or care agent to at least one of the plurality of chambers when the control or regulating device detects on the basis of the received and processed detector signal that this at least one chamber is (completely) closed by the cover. Alternatively or additionally, the control or regulating device is configured to interrupt the supply of at least one cleaning agent and/or care agent to the at least one dispensing element of at least one chamber of the plurality of chambers when the control or regulating device detects on the basis of the received and processed detector signal that this at least one chamber is not (completely) closed by the cover.

The control or regulating device is preferably configured to control or regulate at least one of the control elements of the supply device mentioned above, for example, at least one valve, one throttle or one pump, in order to initiate or interrupt the supply of at least one cleaning agent and/or care agent to at least one dispensing element and/or at least one chamber.

A first method for operating a medical or dental cleaning and/or care device for cleaning and/or care of at least one medical or dental instrument is defined in that a cover is moved, in particular being shifted, in order to close a part of an opening in a housing of the cleaning and/or care device through which a plurality of chambers separated from one another can be loaded with medical or dental instruments, so that when at least one chamber of the plurality of chambers has been closed completely, at least one other chamber of the plurality of chambers is not closed completely and in particular can be loaded with a medical or dental instrument through the opening. The medical or dental cleaning and/or care device comprises in particular a cleaning and/or care device as described above.

A second method for operating a medical or dental cleaning and/or care device is defined in that a detector unit detects at least one position of a movable, in particular displaceable, cover, which is configured to close a part of an opening in a housing of the cleaning and/or care device through which a plurality of separated chambers can be loaded with medical or dental instruments and generates a detector signal that is or can be associated with the at least one detected position. The medical or dental cleaning and/or care device comprises in particular a cleaning and/or care device as described above.

The first and second methods for operating a medical or dental cleaning and/or care device can especially preferably be connected to and/or combined with one another.

The control or regulating device that is operatively connected to the detector unit preferably receives and processes the detector signal that is or can be associated with the at least one detected position and controls and/or regulates the supply of at least one cleaning agent and/or care agent to at least one dispensing element and/or at least one of the plurality of chambers on the basis of the received and processed detector signal. In particular, the control or regulating device controls or regulates at least one of the control elements of the supply device mentioned above, for example, at least one valve, one throttle or one pump in order to trigger or interrupt the supply of at least one cleaning agent and/or care agent to at least one dispensing element and/or at least one chamber.

The dispensing elements and/or the plurality of chambers are preferably supplied with at least one cleaning agent and/or care agent sequentially and/or in alternation. One of the dispensing elements and/or one of the plurality of chambers is especially preferably supplied with a cleaning agent and/or care agent, while another dispensing element and/or another chamber is not supplied with a cleaning agent and/or care agent. One of the dispensing elements and/or one of the plurality of chambers is especially preferably supplied with a cleaning agent and/or care agent while another dispensing element and/or another chamber is being loaded with an instrument to be cleaned and/or cared for or while a cleaned and/or cared for instrument is being removed from another dispensing element and/or from another chamber.

These and other embodiments will be described below with reference to the following drawings.

DETAILED DESCRIPTION

Figure 1:
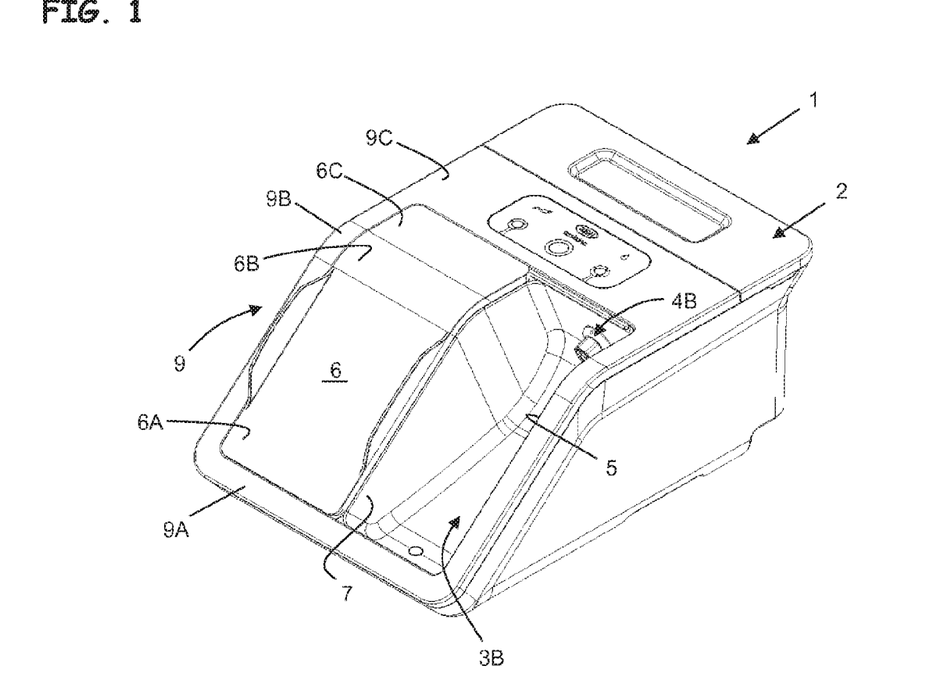
FIG. 1 shows a medical or dental cleaning and/or care device for cleaning and/or care of at least one medical or dental instrument in which a displaceable cover is in a first covering or closed position, in which it closes a part of an opening in a housing of the cleaning and/or care device such that a first chamber for receiving an instrument to be cleaned and/or cared for is completely closed and a second chamber is completely open.
Figure 2:
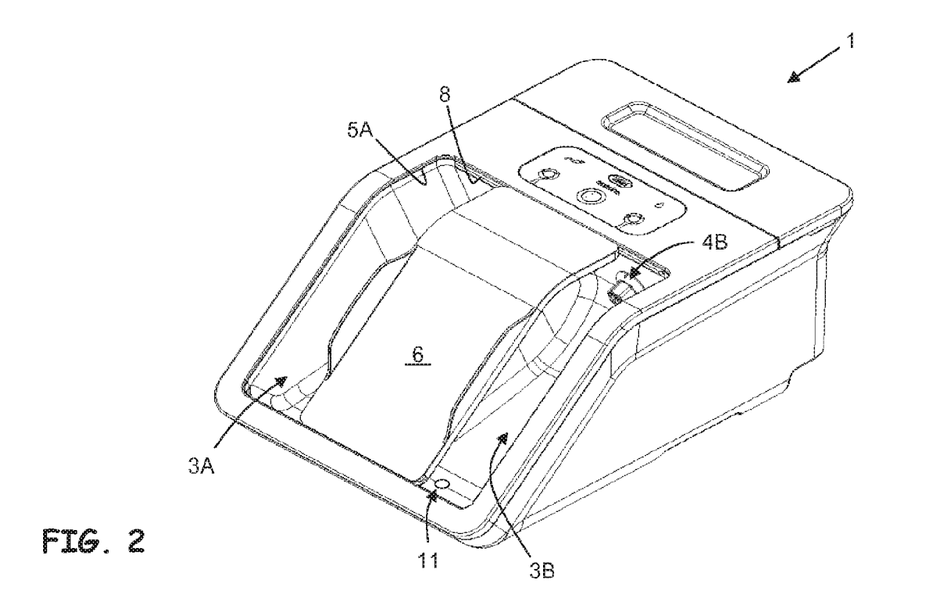
FIG. 2 shows the medical or dental cleaning and/or care device of FIG. 1, wherein the displaceable cover is arranged in a displaced or intermediate position in which none of the plurality of chambers is closed completely by the cover.
Figure 3:
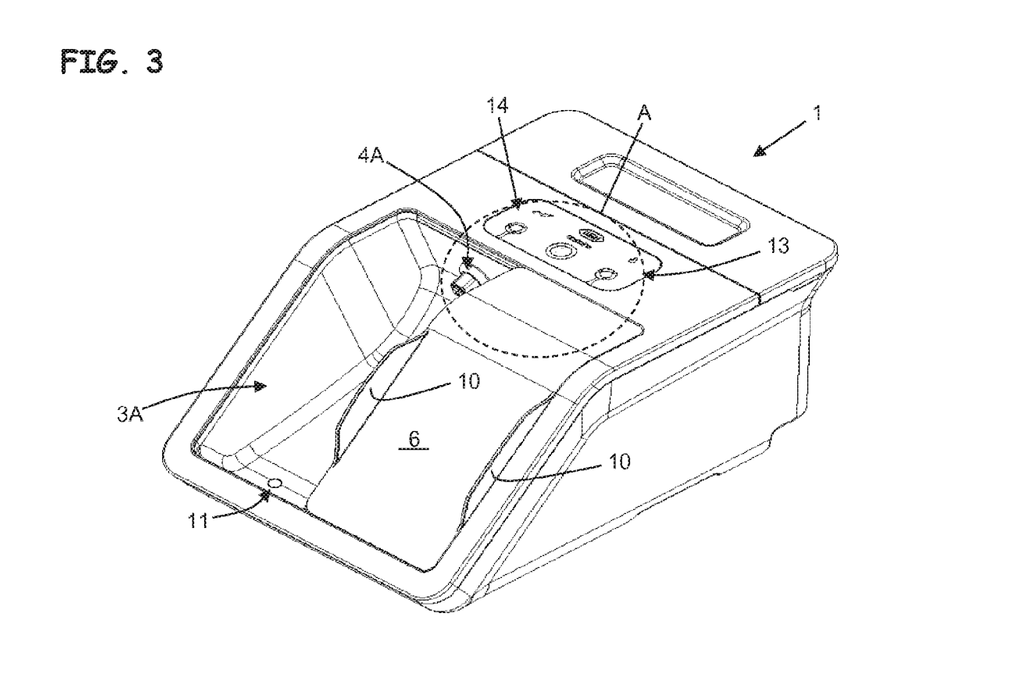
FIG. 3 shows the medical or dental cleaning and/or care device of FIG. 1, wherein the displaceable cover is in a second covering or closing position, in which the first chamber is open completely and the second chamber is closed completely.

The medical or dental cleaning and/or care device 1 illustrated in FIGS. 1-3 for cleaning and/or care of at least one medical or dental instrument comprises a housing 2 and a plurality of chambers 3A, 3B for receiving at least one medical or dental instrument to be cleaned and/or cared for.

The housing 2 preferably comprises a base area or bottom plate, a front face 9 and a plurality of side faces or side walls arranged between the base surface and the front face 9. Preferably at least one (releasable) connection to an energy source and/or to a fluid source is provided on a rear side face. The housing 2 is preferably made of plastic.

The plurality of chambers 3A, 3B in the medical or dental cleaning and/or care device 1 illustrated in FIGS. 1-3 comprise two chambers 3A, 3B, but it is also possible for more than two chambers to be provided, as already described above. Each one of the chambers 3A, 3B has an elongated shape, in particular rectangular, and has a chamber bottom as well as a plurality of side walls. The chamber bottom is preferably arranged at an inclination to the base area of the housing 2, in particular in the direction of an outlet opening 11 for removing (excess) cleaning agent and/or care agent from the chambers 3A, 3B. The chamber bottom is especially preferably inclined from a dispensing element 4A, 4B of the chambers 3A, 3B in the direction of the outlet opening 11.

The chambers 3A, 3B are separated from one another by a wall element 7 wherein the wall element 7 preferably forms one of the plurality of side walls of the chambers 3A, 3B. Each of the chambers 3A, 3B is of such dimensions in particular that at least one medical or dental instrument, preferably a dental handpiece or angle piece can be accommodated in it.

At least one dispensing element 4A, 4B for dispensing at least one cleaning agent and/or care agent into the respective chamber 3A, 3B and/or to the at least one medical or dental instrument that is accommodated in the respective chamber 3A, 3B and is to be cleaned and/or cared for is provided in each chamber 3A, 3B. The at least one dispensing element 4A, 4B is arranged on one of the plurality of side walls of the chambers 3A, 3B and protrudes into the respective chamber 3A, 3B. The at least one dispensing element 4A, 4B is configured in particular as a connector, an extension or a coupling element with at least one borehole or at least one channel for conducting at least one cleaning agent and/or care agent. This borehole or this duct ends in an opening on the surface of the dispensing element 4A, 4B, through which the at least one cleaning agent and/or care agent can be dispensed to a medical or dental instrument which is connected to the dispensing element 4A, 4B. In particular, the cleaning agent and/or care agent can be dispensed through the openings of the dispensing elements 4A, 4B to an interior space of the instrument and/or a component arranged therein, for example, a line, a duct, a tube, a bearing element or a rotary part.

The at least one dispensing element 4A, 4B is connected to a supply device (not shown), which is configured to supply a cleaning agent and/or care agent to the at least one dispensing element 4A, 4B, as already described in detail above. The supply device preferably connects the dispensing elements 4A, 4B to sources for the cleaning agent and/or care agent, for example, to containers for the cleaning agent and/or care agent arranged in or on the cleaning and/or care device 1.

An opening 5 through which the plurality of chambers 3A, 3B can be loaded with medical or dental instruments is provided in the housing 2. The opening 5 extends over all of the plurality of chambers 3A, 3B so that all chambers 3A, 3B are accessible through the opening 5.

In addition, a cover 6 is provided for closing the opening 5 and the plurality of chambers 3A, 3B, in particular during a cleaning and/or care procedure. As can be seen from FIGS. 1-3, only a part of the opening 5 can be closed or covered by the cover 6 so that when at least one chamber 3A, 3B of the plurality of chambers 3A, 3B is completely closed or covered, at least one other chamber 3A, 3B of the plurality of chambers 3A, 3B is not (completely) closed or covered and/or can be loaded through the opening 5 with a medical or dental instrument.

The cover 6 is arranged displaceably in the opening 5, in particular along or parallel to the border 5A of the opening 5. A guide element 8 in the form of a strip, which engages in a groove in the cover 6 and supports and guides the cover 6 is provided on this border 5A of the opening or of the housing 2. The border 5A also delimits the movement of the cover 6 by forming a stop for the cover 6.

The displaceability of the cover 6 is represented by the different positions assumed by the cover 6 in FIGS. 1-3. The cover 6 in FIG. 1 is in a covering or closing position in which the cover 6 completely covers or closes the chamber 3A, in particular so that an instrument accommodated therein can be cleaned and/or cared for while the chamber 3B is open or is not closed and therefore can be loaded with an instrument in particular and/or an instrument can be removed from it. The cover 6 in FIG. 2 is in a displacement or intermediate position in which it does not completely close or cover any of the plurality of chambers 3A, 3B. Therefore, the cover 6 assumes this displacement or intermediate position in particular during displacement from a covering or closing position, for example, on the chamber 3A into another covering or closing position, for example, on the chamber 3B. This covering or closing position on the chamber 3B can be seen in FIG. 3. The cover 6 completely covers or closes the chamber 3B in particular, so that an instrument accommodated therein can be cleaned and/or cared for, while the chamber 3A is open or is not closed and therefore can be loaded with an instrument and/or an instrument can be removed from it in particular.

In addition, at least one handle element 10 for displacement of the cover 6 relative to the opening 5 is provided on the cover 6. The handle element 10 comprises two strips or wings, which protrude from the cover 6 and are arranged in particular on the lateral ends of the cover 6.

The front face 9 of the housing 2, in which the opening 5 is provided has a curvature 9B connecting a first flat front face section 9A and a second flat front face section 9C so that the first front face section 9A and the second front face section 9C are arranged at an angle to one another. The angle amounts to max. 90° but is preferably substantially less, for example, less than 75°, less than 60° or less than 55°. The cover 6 has a shape corresponding to that of the front face 9 with a first flat cover section 6A, a second flat cover section 6C and a bend 6B connecting the first cover section 6A and the second cover 6C.

At least one outlet opening 11 for removing spent or excess cleaning agent and/or care agent that has entered the chambers 3A, 3B during a cleaning and/or care procedure from the chamber 3A, 3B is provided in each of the plurality of chambers 3A, 3B. The outlet opening 11 is provided in particular on a region of the inclined chamber bottom arranged at a low level or close to the base area of the housing 2. The cleaning agent and/or care agent is removed from the chambers 3A, 3B by a suction device provided in the cleaning and/or care device 1, for example.

Figure 4:
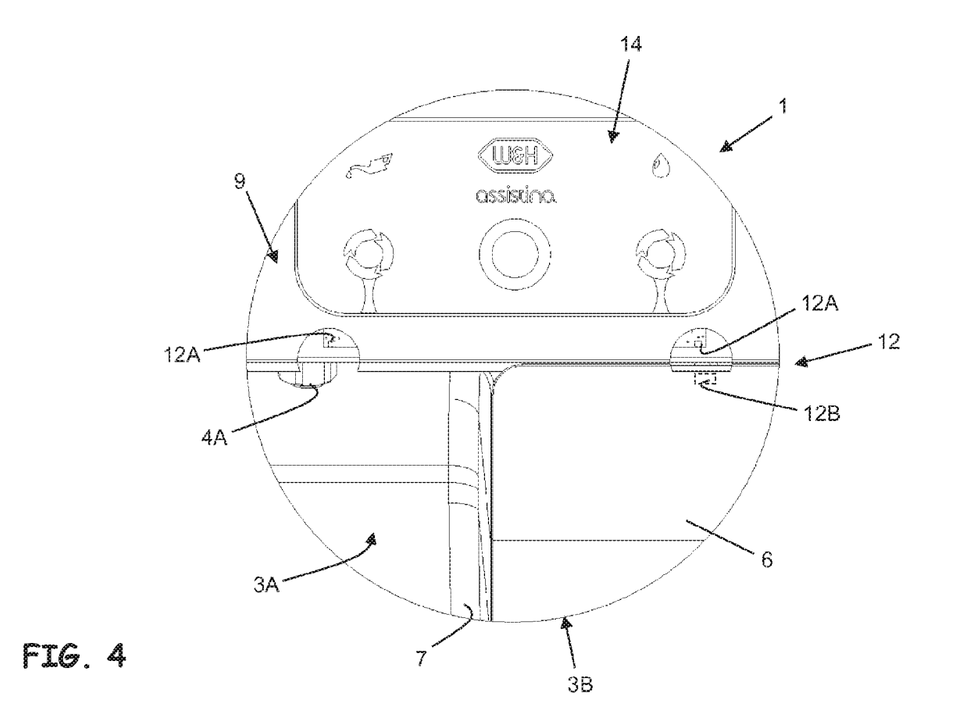
FIG. 4 shows the detail labeled as "A" in FIG. 3 in which an embodiment of a detector unit can be seen, this detector unit being configured to detect at least one position of the cover and to generate at least one detector signal that is or can be associated with a detected position.

FIG. 4 shows the detail of the medical or dental cleaning and/or care device 1 labeled as "A" in FIG. 3, wherein small regions of the front face 9 have been removed to provide a view of parts of a detector unit 12 arranged in the housing 2. The detector unit 12 is configured to detect at least one position of the cover 6, in particular at least one covering or closing position and to generate and/or emit a detector signal that is or can be associated with at least one detected position.

The detector unit 12 comprises at least one part 12B on the cover 6, said part being displaceable jointly with the cover 6. The part 12B is configured as a magnetic element, for example, and/or is arranged in the interior of the cover 6 in particular, for example, being injection molded therein.

The detector unit 12 additionally comprises at least one part 12A, which is arranged to be stationary in or on the housing 2 in relation to the cover 6. As can be seen from FIG. 4, a stationary part 12A, for example, a magnetic sensor, is associated with each one of the plurality of chambers 3A, 3B. If the cover 6 is in a covering or closing position in which, for example, according to FIG. 4 the chamber 3B is covered completely by the cover 6, then the part 12B which has a magnetic element, for example, is close to the part 12A which has a magnetic sensor or Hall sensor, for example, such that the part 12B is detected by the part 12A and a detector signal that is or can be associated with this covering or closing position is generated and/or output. Accordingly, the detector unit 12 is configured to generate and/or output a detector signal that is or can be associated with the covering or closing position when the cover 6 completely closes the chamber 3A in a covering or closing position corresponding to FIG. 1. In the displacement or intermediate position according to FIG. 2, the part 12A does not detect the part 12B, for example, because the distance between these two parts 12A, 12B is too great so that no detection signal is generated.

The medical or dental cleaning and/or care device 1 comprises a control or regulating device 13 which is arranged in the interior of the housing 2 and is operatively connected to the detector unit 12, and is configured to receive and process the detector signal that is or can be associated with the at least one detected position and to control and/or regulate the supply of at least one cleaning agent and/or care agent to at least one dispensing element 4A, 4B and/or at least one of the plurality of chambers 3A, 3B, as described already in detail above. In particular the control or regulating device 13 is configured to allow at least one cleaning agent and/or care agent to be delivered to a dispensing element 4A, 4B arranged in a (completely) closed chamber 3A, 3B and/or not to allow any cleaning agent and/or care agent to be delivered to a dispensing element 4A, 4B arranged in a chamber 3A, 3B that is not (completely) closed.

Finally, an operating or display panel 14 which is operatively connected to the control or regulating device 13 in particular is provided on the housing 2. The panel 14 is configured, for example, to display at least one operating status, operating parameter, a malfunction or a maintenance request. Alternatively or additionally, the panel 14 comprises at least one actuating element, by means of which a user, for example, can set different operating modes of the cleaning and/or care device 1.

The embodiments described or illustrated here serve in particular to illustrate the invention. The features disclosed in an embodiment are therefore not limited to this embodiment but instead may be used individually or combined with one or more features of one of the other embodiments.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

What is claimed is:

1. A medical or dental cleaning and/or care device for cleaning and/or care of at least one medical or dental instrument comprising:
   a housing,
   a plurality of cleaning and/or caring chambers in the housing, each chamber of the plurality of cleaning and/or caring chambers configured for accommodating at least one medical or dental instrument to be cleaned and/or cared for,
   at least one dispensing element in each chamber of the plurality of cleaning and/or caring chambers for dispensing at least one cleaning agent and/or care agent into the respective chamber and/or to the at least one medical or dental instrument that is accommodated in the respective chamber and is to be cleaned and/or cared for,
   a shared opening in the housing through which each chamber of the plurality of cleaning and/or caring chambers can be loaded with at least one medical or dental instrument, and
   a shared single cover movable relative to the shared opening and the plurality of cleaning and/or caring chambers and configured to close each chamber of the plurality of cleaning and/or caring chambers such that when at least one chamber of the plurality of cleaning and/or caring chambers is completely closed, at least one other chamber of the plurality of cleaning and/or caring chambers is not completely closed.

2. The medical or dental cleaning and/or care device according to claim 1, wherein the plurality of cleaning and/or caring chambers is separated by at least one wall element.

3. The medical or dental cleaning and/or care device according to claim 2, further comprising at least one outlet opening for removing cleaning agent and/or care agent from a chamber of the plurality of cleaning and/or caring chambers, wherein the at least one outlet opening is provided in the at least one wall element.

4. The medical or dental cleaning and/or care device according to claim 1, wherein the shared single cover and the plurality of cleaning and/or caring chambers are arranged such that completely closing a first chamber of the plurality of cleaning and/or caring chambers opens a second chamber of the plurality of cleaning and/or caring chambers.

5. The medical or dental cleaning and/or care device according to claim 1, wherein the shared single cover is arranged displaceably in or along the shared opening.

6. The medical or dental cleaning and/or care device according to claim 1, wherein the shared opening is surrounded by a border on which at least one guide element is provided for moving the shared single cover.

7. The medical or dental cleaning and/or care device according to claim 1, wherein the shared opening is surrounded by a border which delimits the movement of the shared single cover.

8. The medical or dental cleaning and/or care device according to claim 1, wherein at least one handle element for moving the shared single cover relative to the shared opening is provided on the shared single cover.

9. The medical or dental cleaning and/or care device according to claim 1, wherein the housing comprises a front face in which the shared opening is provided and which has a first front face section, a second front face section and a curvature which connects the first front face section and the second front face section, so that the first front face section and the second front face section are arranged at an angle to one another and wherein the shared single cover has a shape corresponding to that of the front face with a first covering section, a second covering section and a bend which connects the first covering section and the second covering section.

10. The medical or dental cleaning and/or care device according to claim 1, further comprising at least one outlet opening for removing cleaning agent and/or care agent in each chamber of the plurality of cleaning and/or caring chambers.

11. The medical or dental cleaning and/or care device according to claim 1, further comprising a detector unit, which is configured to detect at least one position of the shared single cover and to generate a detector signal that is or can be associated with at least one detected position.

12. The medical or dental cleaning and/or care device according to claim 11, wherein at least one part of the detector unit is provided on the shared single cover and is jointly movable with the shared single cover.

13. The medical or dental cleaning and/or care device according to claim 11, wherein at least one part of the detector unit is arranged relative to the shared single cover in a stationary position in or on the housing.

14. The medical or dental cleaning and/or care device according to claim 11, further comprising a control or regulating device which is operatively connected to the detector unit and is configured to receive and to process the detector signal that is or can be associated with the at least one detected position and to control and/or regulate a supply of at least one cleaning agent and/or care agent to the at least one dispensing element and/or at least one of the plurality of cleaning and/or caring chambers on the basis of the received and processed detector signal.

15. The medical or dental cleaning and/or care device according to claim 14, wherein the control or regulating device is configured to supply at least one cleaning agent and/or care agent to the at least one dispensing element and/or at least one of the plurality of cleaning and/or caring chambers which is closed by the shared single cover, wherein the control or regulating device detects on the basis of the received and processed detector signal which chamber of the plurality of cleaning and/or caring chambers is closed by the shared single cover.

16. The medical or dental cleaning and/or care device according to claim 14, wherein the control or regulating device detects on the basis of the received and processed detector signal whether at least one chamber of the plurality of cleaning and/or caring chambers is not closed by the shared single cover and wherein the control or regulating device is configured not to supply the at least one cleaning agent and/or care agent to the at least one chamber of the plurality of cleaning and/or caring chambers which is not closed by the shared single cover and/or the at least one dispensing element of said at least one chamber which is not closed by the shared single cover.

17. A medical or dental cleaning and/or care device for cleaning and/or care of at least one medical or dental instrument comprising:
a housing,
a plurality of cleaning and/or caring chambers in the housing, each chamber of the plurality of cleaning and/or caring chambers configured for accommodating at least one medical or dental instrument to be cleaned and/or cared for, at least one dispensing element in each chamber of the plurality of cleaning and/or caring chambers for dispensing at least one cleaning agent and/or care agent into the respective chamber and/or to the at least one medical or dental instrument that is accommodated in the respective chamber and is to be cleaned and/or cared for,
an opening in the housing through which the plurality of cleaning and/or caring chambers can be loaded with medical or dental instruments, and
a cover for closing the opening and the plurality of cleaning and/or caring chambers, wherein only a part of the opening can be closed by the cover so that when at least one chamber of the plurality of cleaning and/or caring chambers is completely closed, at least one other chamber of the plurality of cleaning and/or caring chambers is not completely closed, wherein
at least one handle element for moving the cover relative to the opening is provided on the cover, and wherein
the cover and the plurality of cleaning and/or caring chambers are arranged such that completely closing one chamber of the plurality of cleaning and/or caring chambers through moving the cover by the at least one handle element includes opening of another chamber of the plurality of cleaning and/or caring chambers.

18. The medical or dental cleaning and/or care device according to claim 17, further comprising a detector unit, which is configured to detect at least one position of the cover and to generate a detector signal that is or can be associated with the at least one detected position of the cover, wherein the detector signal is used in control and/or regulation of a supply of at least one cleaning agent and/or care agent to the at least one dispensing element and/or at least one of the plurality of cleaning and/or caring chambers.

19. A medical or dental cleaning and/or care device for cleaning and/or care of at least one medical or dental instrument comprising:
a housing,
a plurality of cleaning and/or caring chambers in the housing, each chamber of the plurality of cleaning and/or caring chambers configured for accommodating at least one medical or dental instrument to be cleaned and/or cared for, at least one dispensing element in each chamber of the plurality of cleaning and/or caring chambers for dispensing at least one cleaning agent and/or care agent into the respective chamber and/or to the at least one medical or dental instrument that is accommodated in the respective chamber and is to be cleaned and/or cared for, an opening in the housing through which the plurality of cleaning and/or caring chambers can be loaded with medical or dental instruments, and a cover for closing the opening and the plurality of cleaning and/or caring chambers, wherein only a part of the opening can be closed by the cover so that when at least one chamber of the plurality of cleaning and/or caring chambers is completely closed, at least one other chamber of the plurality of cleaning and/or caring chambers is not completely closed, wherein the housing comprises a front face in which the opening is provided and which has a first front face section, a second front face section and a curvature which connects the first front face section and the second front face section, so that, the first front face section and the second front face section are arranged at an angle to one another and wherein the cover has a shape corresponding to that of the front face with a first covering section, a second covering section and a bend which connects the first covering section and the second covering section.

20. The medical or dental cleaning and/or care device according to claim 19, wherein the cover and the plurality of cleaning and/or caring chambers are configured such that completely closing one chamber of the plurality of cleaning and/or caring chambers through moving the cover includes opening of another chamber of the plurality of cleaning and/or caring chambers.

* * * * *